(12) United States Patent
Stahlecker

(10) Patent No.: US 6,230,472 B1
(45) Date of Patent: May 15, 2001

(54) PROCESS AND APPARATUS FOR STERILIZING, FILLING AND SEALING CONTAINERS

(75) Inventor: Werner Stahlecker, Goeppingen (DE)

(73) Assignee: Reudiger Haaga GmbH, Altoberndorf (DE)

( * ) Notice: Subject to any disclaimer, the term of this patent is extended or adjusted under 35 U.S.C. 154(b) by 0 days.

(21) Appl. No.: 09/236,565

(22) Filed: Jan. 26, 1999

(30) Foreign Application Priority Data

Feb. 17, 1998 (DE) .............................................. 198 06 520

(51) Int. Cl.⁷ ................................................. B65B 55/04
(52) U.S. Cl. ................ 53/426; 53/468; 53/490; 53/331.5; 53/89
(58) Field of Search .............................. 53/426, 432, 468, 53/490, 471, 167, 510, 331.5, 97, 89, 21; 422/23

(56) References Cited

U.S. PATENT DOCUMENTS

| | | | |
|---|---|---|---|
| 3,486,295 | * 12/1969 | Rausing et al. | 53/89 |
| 3,851,436 | * 12/1974 | Fraser et al. | 53/21 |
| 4,931,261 | * 6/1990 | Jacob | 422/23 |
| 5,656,238 | * 8/1997 | Spencer et al. | 422/23 |
| 5,801,354 | 9/1998 | Kasper. | |

* cited by examiner

Primary Examiner—Peter Vo
Assistant Examiner—Louis K. Huynh
(74) Attorney, Agent, or Firm—Evenson, McKeown, Edwards & Lenahan, P.L.L.C.

(57) ABSTRACT

Containers are sterilized by means of a low-pressure plasma and subsequently filled and sealed in a sterilization chamber.

22 Claims, 1 Drawing Sheet

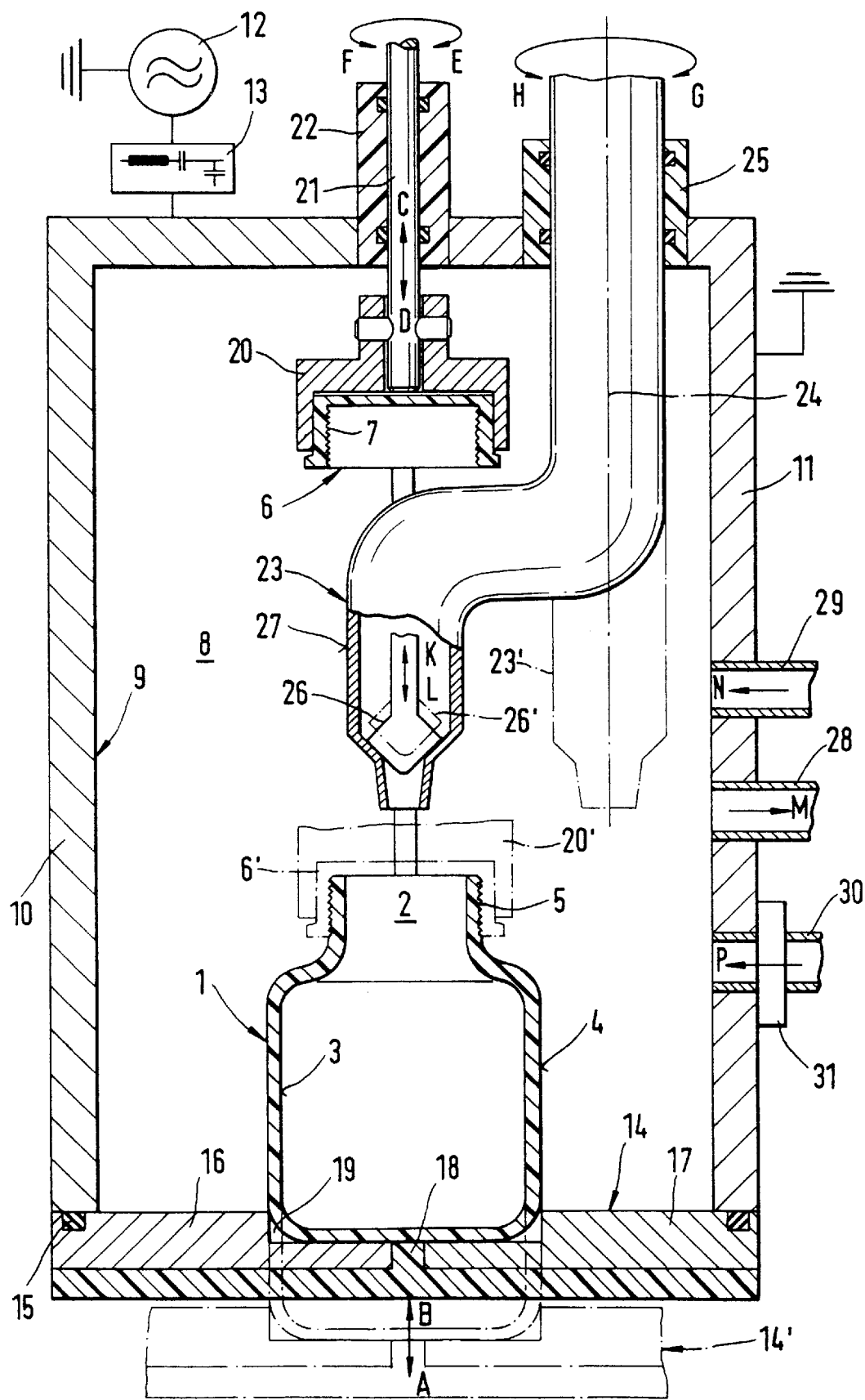

PROCESS AND APPARATUS FOR STERILIZING, FILLING AND SEALING CONTAINERS

BACKGROUND AND SUMMARY OF THE INVENTION

This application claims the priority of German application 198 06 520.5, filed Feb. 17, 1998, the disclosure of which is expressly incorporated by reference herein.

The present invention relates to a process for sterilizing, filling and sealing containers in a sterilization chamber, in which process

- at least one container to be sterilized as well as a closing element arranged at the container is inserted into an opened sterilization chamber,
- the sterilization chamber is subsequently sealed gastight and evacuated.
- at least one gas to be ionized is fed into the sterilization chamber, in which a low-pressure plasma is ignited for a long enough time to effect sterilization,
- the sterilization chamber is subsequently put under a suitable pressure for the purpose of filling the container,
- the container is subsequently filled by means of a filling tube projecting into the sterilization chamber and then closed by means of the closing element, and
- the filled and closed container is finally removed from the reopened sterilization chamber.

In a process of this type (U.S. Pat. No. 5,801,354), it is more incidentally disclosed that, after plasma sterilization, when normal pressure again prevails in the sterilization chamber, the container inside the sterilization chamber can be filled with a liquid. For this, a filling tube is inserted into the sterilization chamber, so that the container is sterilized, filled and sealed in the sterilization chamber. The publication gives no further details on this process. In particular it is not disclosed how the inner walls of the sterilization chamber are made sterile after the container has been placed inside the sterilization chamber, as the known publication lays emphasis on the fact that essentially only the inner surfaces of the containers are sterilized.

It is an object of the present invention to create the conditions whereby at least one container can actually be sterilized in a sterilization chamber by means of a low-pressure plasma, thereafter filled and subsequently closed.

This object has been achieved in accordance with the present invention in that

- in addition to the container and the closing element, all surfaces of the filling tube projecting into the sterilization chamber as well as the inner walls of the sterilization chamber are sterilized,
- and, in order to generate the pressure necessary for the filling of the container, a sterile gas is fed into the sterilization chamber.

The present invention is based on consideration of the fact that after the sterilization chamber is opened in order to insert at least one container and its respective closing element, unsterile surrounding air gets into the sterilization chamber and thus the inner walls of the chamber and the surfaces of the filling tube projecting therein become unsterile.

In the case of the process according to the present invention, the necessary elements for igniting a low-pressure plasma, for example an induction coil or electrodes, are so arranged that, in addition to the container and the closing element, also all surfaces of the filling tube projecting into the sterilization chamber as well as the inner walls of the sterilization chamber are sterilized. As filling cannot take place when the vacuum necessary for sterilizing prevails, it is further taken into account that the ventilation of the sterilization chamber after the sterilization process also takes place in sterile conditions.

An inert gas can be used as a sterile gas, whereby a sterile filter may be provided at the connection to the sterilization chamber. The use of an oxygen-free gas is in any case purposeful, so that oxidation of the filling goods is avoided.

A slight low pressure, normal pressure or even a slight overpressure can be chosen for the filling of the container. A slight overpressure is advantageous in the case of a liquid containing carbon dioxide, as it prevents the liquid from foaming excessively.

In order to accelerate the process, filling of the container can begin before a suitable pressure has been achieved. The filling valve of the filling tube thus opens during ventilation of the sterilization chamber, after sterilization has taken place.

In order that separate devices for applying the closing elements to the sterilization chamber need not be provided, it is provided in a further embodiment of the process of the present invention that the container to be inserted is at first closed by means of the closing element but can be easily opened, and that the closing element of the closed container is removed after it has been inserted in the sterilization chamber in order to uncover the filling opening. This means that devices for handling the closing element in the sterilization chamber are necessary; however, additional transport devices, on the other hand, can be omitted.

In order that the filling tube does not hinder the devices for handling the closing elements, it is further provided that the filling tube can be swivelled from a filling position to an inactive position and back.

These and further objects, features and advantages of the present invention will become more readily apparent from the following detailed description thereof when taken in conjunction with the accompanying drawing.

BRIEF DESCRIPTION OF THE DRAWING

The single drawing FIGURE is a schematic sectional view of a sterilization chamber with a container to be filled, constructed according to a preferred embodiment of the present invention.

DETAILED DESCRIPTION OF THE DRAWING

The new process according to the present invention is applied in cold aseptic filling of containers 1, whereby the sterilization by means of a low-pressure plasma, the filling and the closing all take place in a sterilization chamber 8. The sterilization chamber 8 can take up a plurality of such containers 1, although the following description is based on one single container 1 for the sake of simplicity.

The container 1 has a filling opening 2, which can be closed, for preferably liquid filling goods, for example a beverage. The inner surfaces 3 of the container 1 as well as the outer surfaces 4 at least in the area of the filling opening 2 must be sterilized, whereby in the area of the filling opening 2, for example, an outer screw thread 5 for a closing element 6 is located. The closing element 6 can be a lid with an inner screw thread 7. However, a so-called pull tab is also possible as a closing element, for example for paper cans.

In the case of the following example, the embodiment described concerns only lid-like closing elements 6 having an inner screw thread 7. Further, in the case of the chosen embodiment of the present invention, a non-electroconductive container 1 is provided, although the present invention is not restricted to dielectric containers.

The inner walls 9 of the sterilization chamber 8 are directly formed by electrodes 10 and 11, which are insulated against one another. A high frequency generator 12 is connected by means of an inserted adapter network 13 to the one electrode 10, while the other electrode 11 is grounded. In order to generate the sterilizing plasma, a high frequency, permitted as a radio frequency, can thus be sourced.

The chamber bottom 14 can be raised and lowered according to the directions A and B of the double arrow in order to open and close the sterilization chamber 8. The lowered position is denoted by a dot-dash line and by the reference 14'. The containers 1 can thus be brought into the sterilization chamber 8 and removed again. A ring seal 15 is applied to the chamber bottom 14 to ensure that the sterilization chamber 8 is sealed against gas.

The chamber bottom 14 consists essentially of electrode extensions 16 and 17, which are separated from each other by means of an insulation 18. This insulation 18 extends also from the outside over the entire chamber bottom 14. In the direction towards the sterilization chamber 8, the chamber bottom 14 comprises a container take-up 19 adapted to the cylindrical shape of the container 1. This is purely for the purpose of this embodiment according to the present invention. Other types of transport device (not shown) can, of course, be provided for inserting and removing the containers 1.

In order that separate transport devices do not need to be provided for the closing elements 6, each container 1, before it is placed in the sterilization chamber 8, is, for the purposes of the present invention, at first closed in such a manner that it can be easily opened. Only after the sterilization chamber 8 has been sealed against gas, is the closing element 6 taken from the container 1, in the case of the shown embodiment by means of releasing the inner screw thread 7 from the outer screw thread 5. This is denoted by the rotation directions E and F as well as by the double arrow C-D. The position 6' is denoted by a dot-dash line, and shows which position the closing element 6 takes up during placement of the container 1 in the sterilization chamber 8 and before the filled container 1 is removed from the sterilization chamber 8.

A holding device 20 is provided for handling the closing element 6, which holding device 20 is activated by means of an activating rod 21 from outside the sterilization chamber 8, namely by means of turning and traversing. This activating rod 21 is supported sealed off in an insulated bearing 22.

In the inside of the sterilization chamber 8, a filling tube 23 is further provided, which is offset and which can be swivelled around an axis 24 extending parallel to the axis of the container 1. The inactive position of the filling tube 23 is shown by a dot-dash line and marked with the reference 23'. The relevant rotation directions are denoted by G and H. For filling, the filling tube 23 is brought into the marked position, whereas the filling tube 23 can be swivelled away into the inactive position 23' for the handling of the closing element 6. The filling tube 23 is guided out from the sterilization chamber 8 to the outside also by means of a sealed insulating bearing 25, from where it can be activated.

The filling tube 23 is provided in close proximity to its outflow opening with a valve 26, which can be moved according to the activation directions K and L. The opened position of the valve 26 is denoted with a dot-dash line and marked with the reference number 26'.

The filling tube 23 comprises outer surfaces 27, which must be sterile for the filling process. The area of the valve 26 accessible from the outside is a part of these outer surfaces 27.

The sterilization chamber 8 is provided with a connection 28 to a vacuum pump (not shown), so that the sterilization chamber 8 can be evacuated according to arrow direction M. The sterilizing plasma is generated namely by a very low pressure of preferably less than 100 Pa, as then the plasma has such a low temperature that heat-sensitive containers 1 are not damaged.

The sterilization chamber 8 is further provided with a connection 29 for at least one process gas to be ionized, which gas can be fed after evacuation according to the arrow direction N. In this case, preferably hydrogen or helium or a mixture of both can be used. Other inert gases can, of course, be used.

Finally, the sterilization chamber 8 is provided with a connection 30 for sterile gas, by means of which, according to the arrow direction P, the sterilization chamber 8 can be ventilated again after the sterilization process. The ventilation process is necessary before filling and closing of the container 1. The sterile gas can be an inert gas, or it can be made sterile by means of a sterile filter 31. Preferably the sterile gas is an oxygen-free gas, so that the foam formation during filling of the container 1 is reduced.

After the gastight sterilization chamber 8 has been evacuated and after the suitable process gas has been fed in, low-pressure plasma can be ignited by means of the high frequency generator 12, which low-pressure plasma is maintained for a long enough period to effect a sterilization. Apart from the container 1 and the closing element 6, all outer surfaces 27 of the filling tube 23 including the valve 26, as far as they are located inside the sterilization chamber 8, and the inner walls 9 of the sterilization chamber 8 should be made bacteria-free. After the high frequency is switched off, the sterilization chamber 8 is ventilated with a sterile gas by means of a connection 30, namely as long as a suitable pressure has been reached for the filling of the container 1. Thereafter, the container 1 can be closed, in a bacteria-free condition, with the closing element 6 by means of handling the holding device 20. After sterilization, filling and closing have taken place, the container 1 is removed from the sterilization chamber 8 by sinking the chamber bottom 14.

The sterilization chamber 8 is simply one of many possible embodiments of the present invention. All known sterilization chambers and reactors, with which the filling and closing of containers 1 is generally possible, can, of course, be used.

As a variation on the embodiment of the present invention shown in the drawing, it is possible to apply the filling tube 23 not swivelled around an axis 24, but rather to arrange the holding device 20 for the closing element 6 and the filling tube 23, one downstream of the other, in one production line. In such a case, the containers 1 could be fed through the sterilization chamber 8 by means of a transport device (not shown), and then filled and closed one after the other after the sterilization process.

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

What is claimed is:

1. A process for sterilizing, filling and closing containers in a sterilization chamber comprising the sequential steps of:

placing at least one container to be sterilized as well as a container closing element into an open sterilization chamber having walls formed by electrodes insulated with respect to one another, closing the sterilization chamber gastight and evacuating same, feeding at least one gas to be ionized into the sterilization chamber, igniting a low-pressure plasma in the sterilization chamber for a predetermined time to effect direct sterilization of surfaces of the container by connecting a high frequency generator to one of the electrodes forming the walls of the chamber while another of said walls is grounded, putting the sterilization chamber under a suitable pressure for filling the container, filling the container by a filling tube projecting into the sterilization chamber and then closing the container by the closing element, opening the sterilization chamber, and finally removing the filled and closed container from the reopened sterilization chamber, wherein, in addition to the container and the closing element, all surfaces of the filling tube projecting into the sterilization chamber as well as inner walls of the sterilization chamber are sterilized by the ignited low pressure plasma, and wherein, in order to generate the pressure necessary for the filling of the container, a sterile gas is fed into the sterilization chamber.

2. A process according to claim 1, wherein a slight overpressure is provided as a suitable pressure for filling the container.

3. A process according to claim 2, wherein the closing element is positioned to temporarily close the container when the container is placed into the sterilization chamber, and wherein the closing element is removed from the temporarily closed container, after it has been brought into the sterilization chamber, in order to uncover a container filling opening.

4. A process according to claim 2, wherein the filling tube can be swivelled between a filling position and an inactive position.

5. A process according to claim 1, wherein the filling of the container is begun before the suitable pressure has been reached.

6. A process according to claim 5, wherein the closing element is positioned to temporarily close the container when the container is placed into the sterilization chamber, and wherein the closing element is removed from the temporarily closed container, after it has been brought into the sterilization chamber, in order to uncover a container filling opening.

7. A process according to claim 5, wherein the filling tube can be swivelled between a filling position and an inactive position.

8. A process according to claim 1, wherein the filling tube can be swivelled between a filling position and an inactive position.

9. A process according to claim 1, wherein the container closing element is a separate lid which is detachably attachable to the container.

10. A process according to claim 9, wherein said lid is a threaded lid having an inner screw thread which engages over an exterior screw thread of the container.

11. A process for sterilizing, filling and closing containers in a sterilization chamber comprising the sequential steps of:

placing at least one container to be sterilized as well as a container closing element into an open sterilization chamber, closing the sterilization chamber gastight and evacuating same, feeding at least one gas to be ionized into the sterilization chamber, in which a low-pressure plasma is ignited for a predetermined time to effect sterilization, putting the sterilization chamber under a suitable pressure for filling the container, filling the container by a filling tube projecting into the sterilization chamber and then closing the container by the closing element, opening the sterilization chamber, and finally removing the filled and closed container from the reopened sterilization chamber, wherein, in addition to the container and the closing element, all surfaces of the filling tube projecting into the sterilization chamber as well as inner walls of the sterilization chamber are sterilized by the ignited low pressure plasma, wherein in order to generate the pressure necessary for the filling of the container, a sterile gas is fed into the sterilization chamber, and wherein the sterile gas used is an oxygen-free gas.

12. A process according to claim 11, wherein the filling of the container is begun before the suitable pressure has been reached.

13. A process according to claim 12, wherein the closing element is positioned to temporarily close the container when the container is placed into the sterilization chamber, and wherein the closing element is removed from the temporarily closed container, after it has been brought into the sterilization chamber, in order to uncover a container filling opening.

14. A process according to claim 11, wherein the closing element is positioned to temporarily close the container when the container is placed into the sterilization chamber, and wherein the closing element is removed from the temporarily closed container, after it has been brought into the sterilization chamber, in order to uncover a container filling opening.

15. A process according to claim 11, wherein the filling tube can be swivelled between a filling position and an inactive position.

16. A process for sterilizing, filling and closing containers in a sterilization chamber comprising the sequential steps of:

placing at least one container to be sterilized as well as a container closing element arranged at the container into an open sterilization chamber, closing the sterilization chamber gastight and evacuating same, feeding at least one gas to be ionized into the sterilization chamber, in which a low-pressure plasma is ignited for a predetermined time to effect sterilization, putting the sterilization chamber under a suitable pressure for the purpose of filling the container, filling the container by a filling tube projecting into the sterilization chamber and then closing the container by the closing element, and finally removing the filled and closed container from the reopened sterilization chamber, wherein, in addition to the container and the closing element, all surfaces of the filling tube projecting into the sterilization chamber as well as the inner walls of the sterilization chamber are sterilized, wherein in order to generate the pressure necessary for the filling of the container, a sterile gas is fed into the sterilization chamber, wherein the closing element is positioned to temporarily close the container when the container is placed into the sterilization chamber, and wherein the closing element is removed from the temporarily closed container, after it has been brought into the sterilization chamber, in order to uncover a container filling opening.

17. A process according to claim 16, wherein the filling tube can be swivelled between a filling position and an inactive position.

18. Apparatus for sterilizing, filling and closing containers in a sterilization chamber comprising:

a sterilization chamber having walls formed by electrodes insulated with respect to one another, means for placing at least one container to be sterilized as well as a container closing element into the open sterilization chamber, means for closing the sterilization chamber gastight and evacuating same, means for feeding at least one gas to be ionized into the sterilization chamber, means for igniting a low-pressure plasma in the sterilization chamber for a predetermined time to effect direct sterilization of surfaces of the container by connecting a high frequency generator to one of the electrodes forming the walls of the chamber while another of said walls is grounded, means for putting the sterilization chamber under a suitable pressure for filling the container, means for filling the container including a filling tube projecting into the sterilization chamber, means for closing the container by the closing element, means for opening the sterilization chamber, and means for finally removing the filled and closed container from the reopened sterilization chamber, wherein, in addition to the container and the closing element, all surfaces of the filling tube projecting into the sterilization chamber as well as inner walls of the sterilization chamber are sterilized by the ignited low pressure plasma, and wherein, in order to generate the pressure necessary for the filling of the container, a sterile gas is fed into the sterilization chamber.

19. Apparatus for sterilizing, filling and closing containers in a sterilization chamber comprising:

a sterilization chamber, means for placing at least one container to be sterilized as well as a container closing element into the open sterilization chamber, means for closing the sterilization chamber gastight and evacuating same, means for feeding at least one gas to be ionized into the sterilization chamber, in which a low-pressure plasma is ignited for a predetermined time to effect sterilization, means for putting the sterilization chamber under a suitable pressure for filling the container, means for filling the container including a filling tube projecting into the sterilization chamber, means for closing the container by the closing element, means for finally removing the filled and closed container from the reopened sterilization chamber, wherein, in addition to the container and the closing element, all surfaces of the filling tube projecting into the sterilization chamber as well as inner walls of the sterilization chamber are sterilized by the ignited low pressure plasma, wherein, in order to generate the pressure necessary for the filling of the container, a sterile gas is fed into the sterilization chamber, and wherein the sterile gas used is an oxygen-free gas.

20. Apparatus for sterilizing, filling and closing containers in a sterilization chamber comprising:

a sterilization chamber, means for placing at least one container to be sterilized as well as a container closing element into the open sterilization chamber, means for closing the sterilization chamber gastight and evacuating same, means for feeding at least one gas to be ionized into the sterilization chamber, in which a low-pressure plasma is ignited for a predetermined time to effect sterilization, means for putting the sterilization chamber under a suitable pressure for filling the container, means for filling the container including a filling tube projecting into the sterilization chamber, means for closing the container by the closing element, means for finally removing the filled and closed container from the reopened sterilization chamber, wherein, in addition to the container and the closing element, all surfaces of the filling tube projecting into the sterilization chamber as well as inner walls of the sterilization chamber are sterilized by the ignited low pressure plasma, wherein, in order to generate the pressure necessary for the filling of the container, a sterile gas is fed into the sterilization chamber, and wherein the filling tube swivels between a filling position and an inactive position.

21. An apparatus for sterilizing, filling and closing containers in a sterilization chamber comprising:

a sterilization chamber, means for placing at least one container to be sterilized as well as a container closing element into the open sterilization chamber, means for closing the sterilization chamber gastight and evacuating same, means for feeding at least one gas to be ionized into the sterilization chamber, in which a low-pressure plasma is ignited for a predetermined time to effect sterilization, means for putting the sterilization chamber under a suitable pressure for filling the container, means for filling the container including a filling tube projecting into the sterilization chamber, means for closing the container by the closing element, means for finally removing the filled and closed container from the reopened sterilization chamber, wherein, in addition to the container and the closing element, all surfaces of the filling tube projecting into the sterilization chamber as well as inner walls of the sterilization chamber are sterilized by the ignited low pressure plasma, wherein, in order to generate the pressure necessary for the filling of the container, a sterile gas is fed into the sterilization chamber, and wherein the container closing element is a separate lid which is detachably attachable to the container.

22. An apparatus according to claim 21, wherein said lid is a threaded lid having an inner screw thread which engages over an exterior screw thread of the container.

* * * * *